United States Patent [19]

Gatfield et al.

[11] Patent Number: 5,468,627

[45] Date of Patent: Nov. 21, 1995

[54] PROCESS OF PREPARING BUTYRIC ACID OR 2- OR 3-METHYLBUTYRIC ACID BY OXIDIZING THE CORRESPONDING BUTANOLS WITH GLUCONOBACTER ROSEUS IAM 1841 OR IFO 3990

[75] Inventors: Ian Gatfield, Hoexter; Theodor Sand, Holzminden, both of Germany

[73] Assignee: Haarmann & Reimer GmbH, Holzmiden, Germany

[21] Appl. No.: 27,915

[22] Filed: Mar. 8, 1993

Related U.S. Application Data

[63] Continuation of Ser. No. 691,164, Apr. 24, 1991, abandoned, which is a continuation of Ser. No. 180,419, Apr. 12, 1988, abandoned.

[30] Foreign Application Priority Data

Apr. 24, 1987 [DE] Germany .................. 37 13 688.2

[51] Int. Cl.$^6$ ..................... C12P 7/52; C12N 1/20
[52] U.S. Cl. ................ 435/141; 435/823; 435/252.1
[58] Field of Search ..................... 435/141, 140, 435/822, 823, 136, 252.1

[56] References Cited

U.S. PATENT DOCUMENTS

| 4,400,468 | 8/1983 | Faber ........................... 435/142 |
| 4,826,768 | 5/1989 | Chou ........................... 435/146 |

OTHER PUBLICATIONS

Comprehensive Biotechnology: Principles, Applications and Regulations of Biotechnology in Industry, Agriculture and Medicine, vol. 3, M. Moo–Young, Edit., Pergamon Press, 1985, pp. 965–981.

IAM Catalogure of Strains 1993, First Edition, Microbial and Microalgal Research Center, Institute of Applied Microbiology, University of Tokyo, Japan, pp. 84–86, 421, 422 and 430.

Ley et al., *Bacteriol. Rev.*, vol. 28, pp. 164–180, 1964.

Bergey's Manual of Determinative Bacteriology 8th ed., 1974, pp. 252–253.

ATCC Catalogue of Bacteria, 1992, p. 156.

List of Cultures, 1984, Seventh Edition, Institute for Fermentation, Osaka (wtih full addresses).

Ohta et al, J. Org. Chem., 1982 vol. 47, pp. 2400–2404.

Patent Abstracts of Japan, Band 8, Nr. 232 (C–248) [1669] 25. Oktober 1984; & JP–A–59–113 891 (Mitsubishi Rayon) 30.06. 1984.

Journal of Organic Chemistry, vol. 47, Nr. 12, 4. Juni 1982, pp. 2400–2403, American Chemical Society, Easton, Pa., US; H. Ohta et al.

"Enantiotopically selective oxidation of alpha, omega–diols with the enzyme system of microorganisms".

*Primary Examiner*—Irene Marx
*Attorney, Agent, or Firm*—Sprung Horn Kramer & Woods

[57] ABSTRACT

Disclosed is a process for the preparation of aliphatic carboxylic acids by microbial oxidation of alcohols with relatively long, optionally branched C chains by means of atmospheric oxygen, in which the bacteria species *Gluconobacter roseus* is used as the microorganism. Contemplated is the use of *Gluconobacter roseus* strain IAM 1841 to oxidize n-butanol, isobutanol, 2-methylbutanol and 3-methylbutanol to the corresponding acids. Also contemplated is the use of *Gluconobacter roseus* strain IFO 3990 to oxidize isobutanol, 2-methylbutanol and 3-methylbutanol to the corresponding acids.

7 Claims, No Drawings

PROCESS OF PREPARING BUTYRIC ACID OR 2- OR 3-METHYLBUTYRIC ACID BY OXIDIZING THE CORRESPONDING BUTANOLS WITH GLUCONOBACTER ROSEUS IAM 1841 OR IFO 3990

This application is a continuation of Ser. No. 07/691,164, filed Apr. 24, 1991, now abandoned, which is a continuation of Ser. No. 07/180,419, filed Apr. 12, 1988, now abandoned.

It is known that a cetic acid can be prepared by microbial oxidation of dilute ethanol by means of atmospheric oxygen. Bacteria of the species Acetobacter are used as microorganisms in this preparation (see, for example, Ullmanns Encyclopädie der technischen Chemie (Ullmann's Encyclopaedia of Industrial Chemistry), 4th edition, Volume 11, pages 41 et seq.). It is furthermore known that fusel alcohols, that is to say alcohols with a relatively high carbon number and an optionally branched C chain, are toxic to Acetobacter and therefore can be oxidized microbially to the corresponding carboxylic acids only slowly and in poor yields, if at all. Thus, Ley & Kersters, Bacteriol. Rev. 28, 164 (1964) show that the rates at which the microbial oxidation of isobutyl alcohol and propanol proceed are in a ratio of 3:100. In "Comprehensive Biotechnology", Volume 3, issued by: Murray Moo-Young, published by Pergamon Press 1985, F. H. Sharpell states in chapter 47, "Mikrobial Flavors and Fragrances" on page 971 that although microbial oxidation of isopentyl alcohol is theoretically possible, no microorganism is as yet known which is in fact capable of oxidizing isopentyl alcohol to 3-methylbutyric acid.

Surprisingly, it has now been found that fusel alcohols can also be oxidized microbially to the corresponding carboxylic acids under mild conditions and without the addition of expensive precipitated fermentation additives if a certain bacteria species, namely the species Gluconobacter, is used. Using this bacteria species, it is possible to oxidize fusel alcohols, that is to say alcohols with relatively long, optionally branched C chains, to the corresponding carboxylic acids at high rates and with excellent yields.

The invention therefore relates to a process for the preparation of aliphatic carboxylic acids with relatively long, optionally branched C chains by microbial oxidation of alcohols with relatively long, optionally branched C chains by means of atmospheric oxygen, which is characterized in that the bacteria species Gluconobacter roseus is used as the microorganism.

All the commercially available strains of Gluconobacter roseus are suitable for use in the process according to the invention; the following may be mentioned as examples of such commercially available strains: the strain Number IFO 3990 in the "List of Cultures" ( 1984 ) of the Institute of Fermentation 17-85 Juso-honmachi 2-chome Yodogawa-Ku-; Osaka/Japan, and the strain identified by the number IAM 1841 of the catalogue of the Institute of Applied Microbiology, University of Tokyo/1-1, 1-chome, Yayoi, Bunkyo-ku Tokyo 113 Japan.

Possible alcohols with relatively long, optionally branched C chains are preferably saturated and unsaturated alcohols which have 3 to 10 C. atoms in the chain and are optionally substituted by one or more $C_1$–$C_3$-alkyl groups. Samples of Gluconobacter roseus IFO 3990 and IAM 1841 were deposited with the DSM-Deutsch Sammlung von Mikroorganismen und Zellkulturen GmbH, Mascheroder Weg 1b, D-38124 Braunschweig, Germany under accession numbers DSM 9364 and DSM 9363, respectively, on Aug. 9, 1994, under the provisions of the Budapest Treaty.

The process according to the invention is preferably carried out as follows:

The microorganism Gluconobacter roseus to be used according to the invention is first cultured in a customary culture medium in the manner customary for culture of microorganisms. As soon as a sufficient germ count is reached in the culture medium, the alcohol to be oxidized is added to this. The amount of alcohol is advantageously such that the alcohol concentration is 0.1 to 25 g/l of culture broth, preferably 1.5 to 20 g/l of culture broth. When the oxidation has ended, the carboxylic acid is obtained by acidification of the culture broth to a pH of 3 to 1, extraction with a suitable solvent, for example ethyl acetate, and removal of the solvent by distillation.

The microorganism Gluconobacter roseus to be used according to the invention can be cultured in synthetic, semi-synthetic and natural culture media. To prepare the culture medium, glucose, sucrose, mannitol, sorbitol, glycerol, dextrin, starch, vegetable oils and the like can be used as sources of carbon and meat extract, peptones, gluten flour, cottonseed flour, soybean more, peanut flour, fish meal, grain slops, dry yeast, yeast extract, ammonium sulphate, ammonium nitrate, urea and other organic and inorganic nitrogen sources can be used as nitrogen donors. It is also possible to add, if necessary, metal salts, for example sulphates, nitrates, chlorides, carbonates, phosphates and the like of sodium, potassium, magnesium, calcium, zinc and iron, to the culture medium. The culture medium can furthermore contain surface-active agents and the like with foam suppressants, for example silicone oil.

The culture temperature is usually between 18° and 40° C., and is preferably about 30° C. Good results are obtained if the pH of the culture medium is kept constant at a pH of 3.5 to 7, preferably at 4 to 4.5. The pH can be established, for example, by addition of 25% strength aqueous ammonia solution. Culture can take place either in suitable shaking apparatuses or in fermenters with stirring equipment; adequate aeration should be ensured during culture.

The process according to the invention is particularly suitable for the preparation of isobutyric acid, isovaleric acid and 2-methylbutyric acid.

The aliphatic carboxylic acids which can be prepared by the process according to the invention are flavour substances or can be converted by reaction, for example by esterification, into derivatives which can likewise be used as flavour substances (see, for example, "Comprehensive Biotechnology" loc. cit.).

EXAMPLE 1

A solution of 5 g of yeast extract, 3 g of meat peptone and 25 g of mannitol in 1 l of water was sterilized at 121° C. for 20 minutes. After cooling, 300 ml of this solution were inoculated with Gluconobacter roseus and shaken in a 1 l conical flask at 30° C. for 2 days. 0.5 g of isobutanol was then added to the culture medium and the mixture was shaken at 30° C. for a further 3 days.

For working up, the culture broth was acidified, extracted with ethyl acetate and the solvent was distilled off from the extract.

0.44 g of a liquid which, as shown by analysis by gas chromatography, consisted of isobutyric acid to the extent of 91% was obtained.

EXAMPLE 2

The procedure was as in Example 1, with the modifications that instead of 25 g of mannitol, the same amount of sorbitol was used in the preparation of the culture medium, and that the substrate concentration was increased to 10 g of isobutanol/l of culture broth.

The content of isobutyric acid after 3 days was 12 g of isobutyric acid/l of fermentation solution (determined by quantitative high pressure liquid chromatography (HPLC)).

EXAMPLE 3

A 30 l fermenter was charged with 21 l of water, 500 g of mannitol, 100 g of yeast extract, 60 g of meat extract and 5 g of antifoaming agent and was sterilized at 121° C. for 20 minutes. After cooling, the solution was inoculated with 500 ml of a preculture which had been prepared as described in Example 1, and fermentation was carried out at 28° C., an aeration with 15 l of air/minute and a stirring speed of 300 revolutions/minute. After 27 hours, the pH of the culture medium had fallen from 5.7 to 4.2 and the germ count had risen from $7 \times 10^6$/ml of fermentation solution to $6 \times 10^9$/ml of fermentation solution. 315 g of isobutanol, corresponding to a substrate concentration of 15 g/l, were added to this fermentation solution, the aeration was reduced to 2 l of air/minute and the fermentation was continued. After 15 hours, the pH of the fermentation broth had fallen to 3.8. HPLC analysis of the acidified fermentation solution showed an isobutyric acid concentration of 14 g/l.

A 4 l sample of the fermentation broth was acidified to pH 2 with concentrated sulphuric acid and extracted with ethyl acetate. After removal of the solvent from the extract, 48 g of a liquid which, according to analysis by gas chromatography, consisted of isobutyric acid to the extent of 86% were obtained.

EXAMPLE 4

The procedure was as described in Example 3, with the modifications that the aeration was 12 l of air/minute and the culture time was 24 hours. The preculture thus obtained was used to inoculate a 300 l fermenter which had been charged with 180 l of water, 4.5 kg of mannitol, 900 g of yeast extract, 540 g of meat extract and 50 g of antifoaming agent, sterilized and cooled again to room temperature. The culture broth thus obtained was fermented at 28° C. under aeration with 120 l of air/minute and at a stirring speed of 100 revolutions/minute for 25 hours. During this time, the pH of the fermentation solution dropped from 5.5 to 4.1 and the germ count rose from $8 \times 10^8$/ml of fermentation solution to $4 \times 10^9$/ml of fermentation solution. 2.5 kg of isobutanol, corresponding to a substrate concentration of 12.5 g/l, were added to the fermentation broth thus obtained, the aeration was reduced to 22 l of air/minute and fermentation was carried out for a further 20 hours; in this period, the pH fell to 3.8. The concentration of isobutyric acid in the fermentation solution was determined with the aid of HPLC and was 6 g/l after hours and 15 g/l after 20 hours.

EXAMPLE 5

A culture medium with a germ count of $9 \times 10^9$/ml of culture solution and a pH of 4.2 was prepared in a 30 l fermenter by the procedure described in Example 3. 420 of isobutanol, corresponding to a substrate concentration of 20 g/l, were added to this culture medium and fermentation was carried out under the conditions described in Example 3; in this fermentation, however, the pH was kept at the value of 4.2 by addition of 25% strength aqueous ammonia solution. After 15 hours, the concentration of isobutyric acid in the fermentation solution was determined with the aid of HPLC; it was 21 g of isobutyric acid/l of fermentation solution.

A 4 l sample of the fermentation solution was acidified and extracted with ethyl acetate. After removal of the solvent from the extract by distillation, 65 g of a liquid which, according to analysis by gas chromatography, consisted of isobutyric acid to the extent of 94% were obtained.

EXAMPLE 6

The procedure was as described in Example 3, except that instead of the 315 g of isobutanol, 210 g of 2-methylbutanol, corresponding to a substrate concentration of 10 g/l, were now used. The concentration of 2-methylbutyric acid in the fermentation solution was determined with the aid of HPLC after 24 hours; it was 7 g of 2-methylbutyric acid/l.

For working up, the fermentation solution was acidified to pH 2 with concentrated sulphuric acid and extracted with ethyl acetate. After the solvent had been removed from the extract by distillation, 160 g of a liquid which, according to analysis by gas chromatography, consisted of 2-methylbutyric acid to the extent of 72% were obtained.

EXAMPLE 7

The procedure was as described in Example 6, except that instead of the 210 g of 2-methylbutanol, 210 g of isoamyl alcohol, corresponding to a substrate concentration of 10 g/l, were now used.

After fermentation for 15 hours, the concentration of 3-methylbutyric acid/l of fermentation solution was, according to HPLC, 10 g/l; after fermentation for 39 hours, the concentration of 3-methylbutyric acid had risen to 11 g/l.

Working up of the entire fermentation solution gave 178 g of a yellow liquid which, according to analysis by gas chromatography, consisted of 3-methylbutyric acid to the extent of 90%.

EXAMPLE 8

The procedure was as described in Example 1, with the difference that 500 ml of the nutrient medium were used with 5 g of n-butanol, corresponding to a substrate concentration of 10 g/l.

HPLC analysis of the fermentation solution showed a product concentration of 13 g of n-butyric acid/l of fermentation solution.

EXAMPLE 9

0.5 g of geraniol was fermented under the conditions described in Example 1 for 5 days. For working up the fermentation solution, this was acidified to a pH of and extracted with ethyl acetate. After removal of the solvent from the extract by distillation, 0.41 g of a yellow liquid which, according to analysis by gas chromatography, contained 50% of geranium acid were obtained.

EXAMPLE 10

A culture medium was prepared in the manner described in Example 2, but its pH was kept constant at 4.5 by addition of aqueous ammonia solution. 158 g of isoamyl alcohol were added to the culture medium thus obtained and a further 158 g of isoamyl alcohol were metered in continuously in the course of 8 hours. After fermentation for 25 hours, HPLC analysis showed a product concentration of 17 g of 3-methylbutyric acid/l of fermentation solution.

What is claimed is:

1. A process for the preparation of n-butyric acid comprising (a) oxidizing n-butanol with the strain *Gluconobacter roseus* DSM 9363 to produce n-butyric acid and (b) recovering the n-butyric acid produced in (a).

2. A process for the preparation of iso-butyric acid comprising (a) oxidizing iso-butanol with the strain *Gluconobacter roseus* DSM 9363 to produce iso-butyric acid and (b) recovering the iso-butyric acid produced in (a).

3. A process for the preparation of 2-methyl-butyric acid comprising (a) oxidizing 2-methyl-butanol with the strain *Gluconobacter roseus* DSM 9363 to produce 2-methyl-butyric acid and (b) recovering the 2-methyl-butyric acid produced in (a).

4. A process for the preparation of 3-methyl-butyric acid comprising (a) oxidizing 3-methyl-butanol with the strain *Gluconobacter roseus* DSM 9363 to produce 3-methyl-butyric acid and (b) recovering the 3-methyl-butyric acid produced in (a).

5. A process for the preparation of iso-butyric acid comprising (a) oxidizing iso-butanol with the strain *Gluconobacter roseus* DSM 9364 to produce iso-butyric acid (b) recovering the iso-butyric acid produced in (a).

6. A process for the preparation of 2-methyl-butyric acid comprising (a) oxidizing 2-methyl-butanol with the strain *Gluconobacter roseus* DSM 9364 to produce 2-methyl-butyric acid and (b) recovering the 2-methyl-butyric acid produced in (a).

7. A process for the preparation of 3-methyl-butyric acid comprising (a) oxidizing 3-methyl-butanol with the strain *Gluconobacter roseus* DSM 9364 to produce 3-methyl-butyric acid and (b) recovering the 3-methyl-butyric add produced in (a).

* * * * *

UNITED STATES PATENT AND TRADEMARK OFFICE
CERTIFICATE OF CORRECTION

PATENT NO. : 5,468,627

DATED : November 21, 1995

INVENTOR(S) : Gatfield, et al.

It is certified that error appears in the above-identified patent and that said Letters Patent is hereby corrected as shown below:

Col. 6, line 3  After " acid and before (b) " insert -- and --

Col. 6, line 14  Delete " add " and substitute -- acid --

Signed and Sealed this

Twenty-fifth Day of June, 1996

Attest:

BRUCE LEHMAN

Attesting Officer          Commissioner of Patents and Trademarks